United States Patent [19]

Williams

[11] Patent Number: 5,789,659
[45] Date of Patent: Aug. 4, 1998

[54] MONITORING OF MULTIPLE-ELECTRODE GAS SENSORS

[75] Inventor: David Edward Williams, Abingdon, United Kingdom

[73] Assignee: Capteur Sensors & Analysers Ltd., Didcot, United Kingdom

[21] Appl. No.: 592,407

[22] PCT Filed: Aug. 5, 1994

[86] PCT No.: PCT/GB94/01728

§ 371 Date: Feb. 5, 1996

§ 102(e) Date: Feb. 5, 1996

[87] PCT Pub. No.: WO95/04927

PCT Pub. Date: Feb. 16, 1995

[30] Foreign Application Priority Data

Aug. 5, 1993 [GB] United Kingdom ............... 9316280

[51] Int. Cl.$^6$ ............ G01N 27/12; G01N 31/00; G08B 17/10
[52] U.S. Cl. ............ 73/23.2; 73/31.06; 73/29.01; 73/335.05; 204/411; 204/412; 340/632; 364/498; 364/553
[58] Field of Search .............. 73/23.2, 23.21, 73/24.04, 31.06, 335.05; 340/632, 634; 204/412, 411; 364/498, 553, 576

[56] References Cited

U.S. PATENT DOCUMENTS

| | | | |
|---|---|---|---|
| 3,727,450 | 4/1973 | Luckers | 73/23 |
| 4,457,161 | 7/1984 | Iwanaga et al. | 73/23 |
| 4,502,320 | 3/1985 | Sakai et al. | 73/23 |
| 4,526,028 | 7/1985 | Hübner | 73/23 |
| 4,818,348 | 4/1989 | Stetter | 204/1 T |
| 4,907,441 | 3/1990 | Shurmer | 73/23 |
| 5,034,725 | 7/1991 | Sorensen | 340/632 |
| 5,184,500 | 2/1993 | Krema et al. | 73/23.2 |
| 5,369,975 | 12/1994 | Matter et al. | 73/23.2 |
| 5,481,476 | 1/1996 | Windig | 364/498 |
| 5,526,280 | 6/1996 | Consadori et al. | 364/496 |

Primary Examiner—Hezron E. Williams
Assistant Examiner—J. David Wiggins
Attorney, Agent, or Firm—James B. Middleton

[57] ABSTRACT

A gas sensor, suitable for use under non-steady state conditions, has a gas-sensitive resistor with pairs of electrodes which either have different spacings between the electrodes of a pair, or comprise a pair at the active surface and further pairs buried in the resistor at different distances from the active surface. The sensor can be used in place of a sensor array, and is coupled to a processor for processing the resistance signals to detect and/or measure at least one target gas. The sensor is self-diagnostic, and factors such as relative humidity and ambient oxygen, that can otherwise affect the readings, can be compensated for without the aid of additional sensors for that purpose. An operating line or surface is defined for the expected behavior of the sensor, and the resistance signals from the electrode pairs are processed so at to give information which is then related to the operating line or surface, so as to reveal, in terms of error indications, any malfunction of the sensor and/or the presence of specific constituents of the gas mixture.

17 Claims, 2 Drawing Sheets

MONITORING OF MULTIPLE-ELECTRODE GAS SENSORS

The present invention relates to methods of monitoring multiple electrode resistive gas sensors comprising a gas-sensitive resistor, preferably but not exclusively comprising a semi-conductive oxide material, and having an active surface and a plurality of pairs of electrodes for the purpose of measuring the resistance, with the electrode pairs being different from each other as regards the spacing between the electrodes of the pair or the disposition of the pair within the body of the resistor relative to the active surface, i.e. the external surface in contact with the gaseous atmosphere.

The term "monitoring" is used here in a broad sense to mean making use of the signals from the sensor for any desired purpose, including determination of one or more target gases in a gaseous mixture; making corrections to compensate for factors that would otherwise tend to give rise to errors in the information received by the user; and testing the sensor itself for correct operation. Determination of target gases in a gaseous medium containing more than one target gas comprises detection and/or measurement of those gases. In general, the target gas is a gas capable of causing the electrical resistance of the sensor to vary in response to gas concentration.

A multiple electrode resistive gas sensor is disclosed in the document GB 2 218 523B, which describes a method of detecting and/or measuring at least one gas by exposing an active surface of a gas sensor to the gas or gases, allowing the latter to diffuse through a porous body of the sensor on which the active surface is formed, the body being of a suitable electrically conductive material, and measuring resultant changes in the electrical, conductance of the body material in at least one region of the latter remote from the active surface. For this purpose, electrodes are arranged at suitable positions remote from the active surface.

The document WO92/21018 discloses a multiple electrode sensing device of the above type, which has a plurality of electrodes arranged in pairs, with the electrodes of one pair being spaced apart by a different distance from that by which the electrodes of another pair are spaced apart. The same document discloses that, alternatively, some aspect (such as relative position) of the relationship between the electrodes of a pair and the active surface, is different from one pair of electrodes to the next. Gas composition is determined from the relationship between the resistances across the respective pairs of electrodes.

It is often required that the presence of any one or more of a number of specified gases (commonly referred to as "target" gases) should be determined in a gaseous mixture. Conventional practice is to construct for this purpose an array of discrete gas sensing devices, with each sensor being normally one that is sensitive to a respective one of the target gases. A conventional array of this kind suffers from the fact that each sensor is a separate device, subject to its own manufacturing tolerances and imperfections. As a result, such an array has the serious disadvantage that drift effects occur in practice. Results obtained from the array as a whole tend to be seriously affected by cumulative errors arising in the various devices. This also has the effect that repeatability between arrays tends to be virtually impossible.

An object of the invention is to overcome these drawbacks of sensor arrays.

A further object is to enable a plurality of target gases to be determined (detected, measured) in a mixture of gases, without the disadvantages of conventional sensor arrays.

According to the invention in a first aspect, a method of analysing a gaseous medium using a multiple-electrode resistive gas sensor comprising a resistor having an active surface and a plurality of pairs of electrodes, the electrode pairs being different from each other as regards the spacing between the electrodes of the pair or the disposition of the pair within the resistor relative to the active surface, the gaseous medium containing at least one target gas capable of causing the electrical resistance of the sensor to vary in response to concentration of that gas, is characterised in that the method comprises: taking a resistance signal from each electrode pair with the sensor exposed to the gaseous medium; processing the signals to produce measurements therefrom; and relating the said measurements to a defined operating line or surface so as to determine, by deduction therefrom, a plurality of items of information, with the concentration of each target gas to be detected representing a separate said item, and in that the number of electrode pairs is at least equal to the number of items of information to be obtained.

We have found that a multiple electrode gas sensing device, typically of the kind mentioned above, can be used for the same purpose as a conventional array. Furthermore, we have realised, not only that such a device is the functional equivalent of such an array and can be used, in its place, but it has the major advantage that when this is done, the drift effect mentioned above is to all intents and purposes eliminated.

In addition, not only can a multiple electrode replace a conventional array of discrete sensors for detecting the presence of one or more of a number of target gases in a gaseous mixture, but it also has the advantage that it can be so designed as to provide an optimum solution to the required analytical task.

The operation of a multi-electrode sensor as a functional (though better) equivalent of a conventional array of discrete sensors can be explained theoretically as follows. A sensor array can be considered as a set of devices, numbered with the index j, responding to a mixture of gases, the gases being numbered with the index i. The response of the jth sensor to the ith gas is determined by a coefficient $k_{ij}$, to be determined by calibration. In the simplest case, the response of the devices, ($G_j$ denotes the response of the jth sensor) is considered to be linear in gas concentration, $c_i$, and additive, that is without interaction terms between the different gases, so that $$G_j = \Sigma k_{ij} c_i$$

In order to determine the concentrations of the different gases, the calibration coefficients must first be determined, and the concentrations can then be determined from the responses by solution of the set of simultaneous equations above. Where the response is non-linear then the signal from the sensors must first be linearised, and the above equation set will then apply to the linearised result. Where there are interaction terms (i.e. terms in the products of concentrations of different gases), then more elaborate signal processing methods will be required. Arrays of this kind have also been extensively employed in pattern recognition tasks (e.g. the so-called artificial nose); such an application does not necessarily involve the solution of the above equation set.

In the multi-electrode sensor of the kind disclosed in the document WO92/21018, assuming that the conductivity change is linear in the gas concentration, the response of the jth electrode pair to a single gas in a specific concentration c can be written in the forms:

$$G_j = \alpha_j K_p c$$

in which $K_p$ is a constant characteristic of the response of the sensor material to the gas, and $\alpha_j$ is a coefficient (termed hereafter the response coefficient) which is a product of two factors. One of these depends on the gas, being dependent more particularly on the reactivity of the gas so that it is different for different gases and, for any given gas, varies strongly with the temperature. The other factor depends on the geometry of the sensor, e.g. in a planar device, the inter-electrode gap and the sensing layer thickness.

When multiple gases are present, then, with i gases, for each electrode pair, j, of a multiple electrode sensor:

$$G_j = \Sigma \alpha_{i,j} K_{p,j} C_i$$

This result demonstrates that the multi-electrode sensor behaves just like a sensor array,with the important difference that the response coefficients, $\alpha_{i,j}$, can be tailored by adjustment of the sensor geometry and gas reaction kinetics (by change of the temperature), and are, furthermore, related to one another in a well-defined way, which should not change during the operation of the sensor..

Finally, the use of such multiple electrode sensors allows the creation of an array of multiple devices, each of which is operated at a different temperature, or is made of a different sensor material, or has a different geometry. Some devices may have a porous but inert coating over the active sensor layer; in others, this coating might be treated with a catalyst to promote decomposition of one or more of the gases present; again, a catalyst may be impregnated into the active sensor layer; the active sensor layer may itself be prepared with a graded or layered composition; and the electrode material can be chosen either to be catalytic for decomposition of the gas (e.g. platinum) or inert to the gas (e.g. gold). In all cases, the use of a multiple electrode device produces an output equivalent to that of a sensor array, the important distinction from a conventional array being that the output can be adjusted to match the analytical problem and that malfunctioning of the device can be detected and distinguished from genuine changes in the gaseous composition.

The document WO92/21018, mentioned above, discusses the concept of a multi-electrode resistive gas sensor and its operating line, or operating surface. This operating line or surface is defined by the response of the different electrodes of the sensor, and can be used to deduce the composition of a gaseous mixture, in the case where the resistance of the sensor material varies in response to the concentration of more than one gas; or to indicate conditions in which the sensor indication becomes unreliable; or both. A distinction between gases, or a deduction of impending failure of the sensor, can be made if a conductivity gradient exists through the sensor body. This conductivity gradient arises as a consequence of a gradient of gas concentration, together with the variation of conductivity of the material with changing gas concentration.

In the steady state, that is to say in the condition under which the gas composition does not vary with time, or varies only slowly in comparison with the natural time constants associated with the sensor response, a concentration gradient can arise as a result of the coupled effects of diffusion and chemical reaction within the sensor body. The document WO92/21018 shows how such steady-state signals can be used to define an operating line (or surface) for a multiple-electrode resistive gas sensor, leading to the desired objectives of a self-diagnostic device capable of distinguishing the effects of different gases in the mixture.

In practice, the gaseous environment to which a sensor is exposed tends to be in a non-steady state rather than a steady state. In order to make use of a monitoring technique that relies on readings taken in the steady state, it is therefore necessary to provide some means for putting the immediate environment of the sensor into a steady state. This is inconvenient and often impossible.

Another object of the invention is to provide a monitoring method (as defined above) for multiple electrode gas sensors which can be used at all times, both when the environment is in a steady state and when it is in a non-steady state.

According to the invention in a second aspect, a method of monitoring a gas sensor comprising a gas-sensitive resistor having an active surface and a plurality of pairs of electrodes, the electrode pairs being different from each other as regards the spacing between the electrodes of the pair or the disposition of the pair within the resistor relative to the active surface, comprising the steps of: defining an operating line or operating surface for operation of the sensor in a gaseous medium at the active surface; exposing the sensor to a said medium; processing the signals from each electrode pair that represent the resulting resistance of the resistor between the electrodes of that pair, so as to produce measurements therefrom defining an operating point, and relating the operating point to the defined operating line or surface, whereby the presence of an error in the detection of at least one gas in the said medium can be deduced from any shift of the operating point with respect to the defined operating line or surface, is characterised in that the operating line or surface is defined for, operation under non-steady state conditions, the sensor being exposed to the medium under non-steady or steady state conditions.

The invention greatly enhances the usefulness and field of application of multiple electrode sensors, in particular by enlarging the scope for using a single sensor where previously an array of sensors was needed, besides giving other advantages which will appear from the discussion that follows, with examples, and with reference to the accompanying drawings, in which.

In this description, the concept of a generalised, non-steady-state operating line or surface will be discussed. It may be shown that the different electrodes of a multiple electrode resistive gas sensor show a different time variation of the resistance response when the sensor is exposed to a rapid variation of gas concentration (such as a step change). In the case of a planar sensor with electrodes disposed at different spacings at the base of the sensing layer, all of the electrode pairs will indicate a resistance variation which finally levels out to a value dependent upon the new gas concentration.

However, for an electrode pair which is closely spaced, the resistance change will be slower than that for an electrode pair which is widely spaced. The reason is that the closely spaced pair of electrodes samples only the resistance of the sensor material close to the base of the sensing layer. The delay arises because of the time it takes for the gas concentration change to penetrate through the layer to the base. The effect of chemical reactions of the gas will be to alter the form of the resistance variation generally slowing down the response. There will however be a delay in the response of the closely spaced electrodes, whether or not there is any chemical reaction, simply because there is an inevitable delay associated with the effect of diffusion of the gas through the sensor body.

The methods described herein can therefore be used to verify the operation of the devices in which the gas is not decomposed upon diffusion through the sensor body, but is unaffected or simply adsorbed upon the active sensor surface. Such a class of devices may include semiconducting oxide devices with surface modified by the addition of precious metals so as to operate at room temperature.

Figure 1:
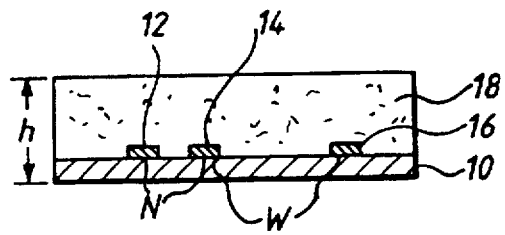
FIG. 1 is a diagrammatic representation of one form of multiple electrode resistive gas sensor.

Referring to FIG. 1, this shows a multiple electrode resistive gas sensor of a planar type, comprising a flat substrate 10 impervious to a target gas or gases. Three electrodes 12, 14 and 16 are arranged on the substrate, to define a first electrode pair N consisting of the electrodes 12 and 14, and a second electrode pair W consisting of the electrodes 14 and 16. The spacing between the electrodes 12 and 14 is narrower than that between the electrodes 14 and 16, and for convenience the pairs N and W can be referred to as the narrow or narrowly-spaced pair and the wide or widely-spaced pair, respectively.

Overlaid on the substrate 10 is a gas sensing layer or resistor 18 of a suitable electrically resistive, gas sensitive, semi-conducting material, in which all the electrodes are accordingly buried. The spacings in the electrode pairs N and W are narrow and wide, respectively, in relation to the overall thickness h of the sensor, indicated in FIG. 1.

It should be noted that the layer 18 will be assumed in this example to be such that its resistance decreases with increasing concentration of the target gas. It might equally well be such that its resistance increases as the concentration increases.

Figure 2:
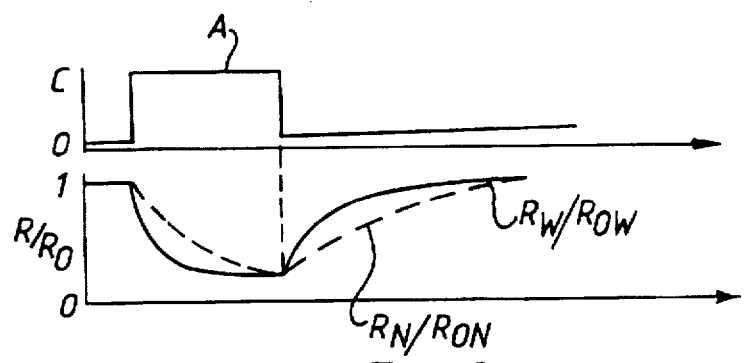
FIG. 2 is a composite diagram showing the response of the sensor of FIG. 1 to changes in concentration of a gas.

FIG. 2 shows, for gas concentration C plotted against time to give a trace A (which for simplicity shows a simple square pulse, though it may have a more complex form), the curves of $R_W/R_{OW}$ (in a full line) and $R_N/R_{ON}$ (in a broken line), where R is sensor resistance in response to the concentration C, $R_O$ is the resistance in the absence of the gas, and the suffix W or N represents the electrode pair between which the resistance concerned is measured.

Overall, the time scale for the response is defined by the characteristic time $h^2/D$ for diffusion of the gas through the layer 18, where D is the diffusion coefficient of the gas through the layer 18. FIG. 2 shows that the response for the narrow electrode pair N is delayed with respect to that for the wide electrode pair W.

Figure 3:
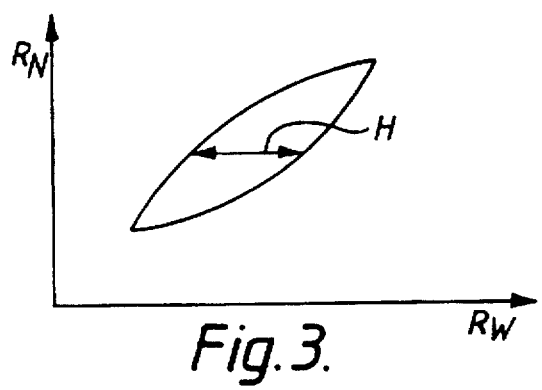
FIG. 3 shows the relationship between the responses at two pairs of electrodes of the same sensor.

In FIG. 3 the resistance $R_N$, measured between the electrodes 12 and 14, is plotted against the resistance $R_W$ measured between the electrodes 14 and 16. FIG. 3 shows that the time variation between these two resistances defines a hysteresis loop, the width H of which is determined by the time delay between the two responses and depends on the amplitude and form of the time variation of the gas pulse (such as that at A in FIG. 2).

Another way of characterising the response of the sensor is to develop the concept of a transfer function that relates the response at one pair of electrodes to that at another pair. This is best illustrated with reference to a sensor having the electrode geometry shown diagrammatically in FIG. 4, which may be called "idealised slab geometry". The person skilled in the art will realise that although in FIG. 4 this geometry is somewhat formalised, it is within the competence of such a person to manufacture a practical sensor of this kind. In addition results obtained with idealised slab geometry can be directly related to those expected for the more common planar geometry exemplified in FIG. 1.

Figure 4:
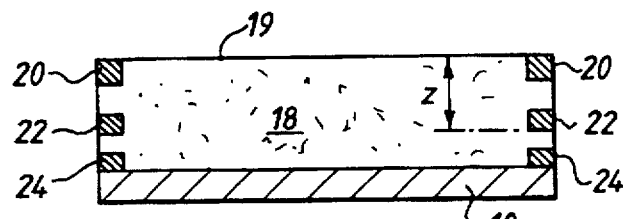
FIG. 4 is a diagrammatic representation of another form of multiple electrode gas sensor.

In FIG. 4, the sensor again has a substrate 10 overlaid by a gas sensing layer 18, these being generally as described above with reference to FIG. 1. A pair of first or outer electrodes 20 are inset into the active surface 19 of the sensing layer 18, so that the electrodes 20 are themselves directly exposed to gas introduced to the sensor. At least one further pair of electrodes is buried within the layer 18. In FIG. 4 there are two of these buried pairs, 22 and 24. The spacing between any one electrode pair and the next (in the direction of the thickness of the layer 18) will be chosen according to the application in which the sensor is intended to be used.

A sinusoidal variation of gas concentration with time will now be considered with respect to a sensor of the kind shown in FIG. 4. This will be called a "stimulus". Any arbitrary temporal gas concentration variation can be expressed as a sum of such sinusoidal variations. The resistance variation measured between the electrodes 20 of the outer pair will then be a measure of the stimulus. The response at any buried electrode pair 22 or 24 will be damped in amplitude and shifted in phase, relative to the signal at the outer electrode pair 20, by an amount which depends upon the product of the frequency of the stimulus and the characteristic diffusion time taken for the change to penetrate to the buried electrode pair in question ($z^2/D$, where z here denotes the depth of the electrode pair below the active surface 19 of the sensor). The ratio of the resistance measured between the buried electrodes (the "signal") to that measured between the electrodes of the outer pair 20 (the "stimulus") is the transfer function of the device. It may be characterised by two numbers, one being the magnitude of the ratio and the other being the phase angle between the signal and the stimulus. Alternatively, the transfer function may be expressed as a complex number, the two numbers characterising it then being real and imaginary parts. The amplitude and phase (or real and imaginary parts) of the transfer function will depend upon the frequency and the amplitude of the periodic gas concentration variation.

A further and interesting point arises if the response of the sensor is non-linear in the gas concentration, as is indeed usual in practice. A typical variation, when the resistance of the material used decreases with increasing concentration of target gas, consists of variation in the conductivity with respect to the square root of the gas concentration. If, on the other hand, resistance increases with increasing gas concentration, then it is typically resistivity that increases with the square root of gas concentration.

Furthermore, when more than one gas is present, there may be cross-terms in the response, such that the sensitivity to one gas is dependent on the concentration of another gas. Such effects in sensitivity to target gases arise, in particular, as a consequence of variations in ambient relative humidity or oxygen partial pressure. Such variations are common. If the sensor response is non-linear in the gas concentration, then a sinusoidal variation of gas concentration will induce components of the response at harmonics of the frequency of concentration variation, the amplitude of such harmonics depending on the response law and sensitivity. A change in the sensitivity would change the relative amplitude of the different harmonics.

If the sensor is exposed to some arbitrary variation of gas concentration with time, the signals available from resistance measurement across the various electrode pairs are analysed as follows. First, the signal from a primary electrode pair (i.e. in a planar sensor the most widely spaced pair such as W in FIG. 1, or, in an idealised slab sensor, the outer pair such as the electrodes 20 in FIG. 4), is analysed as a sum of sinusoidal variations. The process of Fourier transformation is a convenient way of doing this. Alternatively, the signal can be passed through a set of filters having different pass-band frequencies.

The next step is to analyse in the same way the signals from the secondary electrode pair or pairs (i.e. in a planar sensor the narrower electrode pairs such as N in FIG. 1, or in an idealised slab sensor the buried electrode pairs such as 22 and 24 in FIG. 4). The transfer functions for the secondary electrode pairs are then calculated relative to the primary electrode pair, and can be displayed as a function of frequency.

Alternatively, a cross-correlation function between the two outputs of the device, given by:

$$R_{(\tau)} = \frac{1}{T} \int_0^T f(t)g(t+\tau)dt$$

can be calculated, where t is time, T is the time over which the measurement is evaluated, and $\tau$ is delay time.

The cross-correlation function shows a maximum value at the characteristic delay time, different for each secondary electrode pair, i.e. each buried electrode pair or electrode pair of smaller spacing, for diffusion of the gas through the material. The delay time should evidently remain unchanged if the sensor characteristics are unchanged. Similar standard methods of analysis of time-series data can be used to identify the harmonic components of the signal variation, and hence to observe any change in the response law of the material.

These different methods of examination of the time-dependent output of a multi-electrode sensor can be used to check the continued reliable operation of a sensor, or to distinguish the composition of a mixture containing a number of different gases which differ in their rate of diffusion through the sensor body, or both.

The key concept is that of the non-steady-state operating line or operating surface. Thus, when a sensor is exposed to a pulse of gas (for example, for the purposes of testing), then the operating line, for a sensor having two electrode pairs, may be defined as a plot of the magnitude of the hysteresis as a function of the extreme value obtained during the gas exposure by one of the measured resistances. For a sensor having more than two electrode pairs, the operating surface can be defined by the values of the hysteresis obtained on each secondary electrode pair when the resistance is plotted against that for the primary electrode pair, as a function again of the extreme value of resistance obtained on the primary electrode pair.

In the case where the variation of gas response with time is more complicated, an operating surface can be defined as the expected variation of the amplitude and phase of the transfer functions of the different electrode pairs, as a function of the frequency of the stimulus.

It will now be appreciated by the person skilled in the art that a sensor can readily be designed (for instance by control of the thickness, internal surface area and porosity of its sensing layer) in such a way as to have characteristic response times for the gases of interest falling within a range which is easily measurable; or to have such characteristic response times commensurate with the time scales of expected natural variation of gas composition.

It will also be appreciated that it is possible to use the signals from such a multiple-electrode sensor, firstly to give a prompt warning of the presence of some gas (using the output from electrodes arranged so as to probe the outer part of the sensor layer in immediate contact with the atmosphere); and then, with some delay depending on the design of the sensor and the gases to be detected, to give an indication of the nature of the gases, present or a diagnostic signal, from the delayed response obtained from electrodes probing the parts of the sensor layer remote from the outer surface of the sensor.

The general concept of operating lines or surfaces in a multi-electrode sensor can be applied not only in the steady state, but also in non-steady state situations, to correct for the effect of variations of relative humidity, or of ambient oxygen partial pressure, on the sensor signal. Variations in relative humidity or oxygen partial pressure are the most important sources of interference with the signal provided by gas-sensitive resistors. Such effects are not confined to the semiconducting oxide type of gas-sensitive resistor, but occur with all types, including those based on conducting polymers and phthalocyanines. The effects of variation in relative humidity or oxygen partial pressure are to change the baseline resistance of the device, or the sensitivity of response to a target gas (i.e. the change in conductance or resistance caused by the presence of a given concentration of the target gas present in the atmosphere), or both.

Accordingly, it has generally been assumed hitherto that, for accurate measurement, a second or indeed a third device, which measures ambient relative humidity or oxygen partial pressure, or both, is required in order to derive a correction for the sensitivity or baseline, or both, of the gas sensor.

However, given the concept of a multi-electrode sensor and its non-steady state operating line or surface as discussed above, it will be clear that the problem of interference with the signal by changes in relative humidity and/or oxygen partial pressure can be solved by the invention without recourse to the use of any such additional device for independent measurement of these quantities.

In this connection, the document WO92/21018, mentioned above, describes how mixtures of a reactive gas and an unreactive gas can be resolved with the use of a sensor in which the reactive gas is decomposed as it diffuses through the porous sensor body. Water vapour and oxygen appear to the sensor as unreactive gases, that is to say their concentration in the steady state is uniform throughout the sensor body. The effect of variation of their concentration is to shift the operating line or surface of the multi-electrode sensor in a characteristic fashion, which is different from the effect of poisoning. Indeed, the shift of the operating point of the sensor (i.e. the point at which the coordinates are defined by the measured resistances or conductances from the different electrode pairs), within a coordinate space the axes of which are defined by the quantities to be measured, is characteristic of the influences to which the sensor is exposed.

Poisoning will give a direction and magnitude of shift which is different from that caused by the effects of water vapour or oxygen partial pressure. This is itself different from the direction and magnitude of shift caused by the presence of target gases for which the measurement system has been calibrated. This, again, is different from the effect of gases for which the measurement system has not been calibrated.

Various patterns in the shifting of the operating point of the multi-electrode sensor can therefore be discerned, recognised, and used in any known way to trigger warning signals or to correct the output of the device. This principle of a shifting operating point is illustrated in FIG. 5, purely for simplicity, and shows a steady-state operating line.

Figure 5:
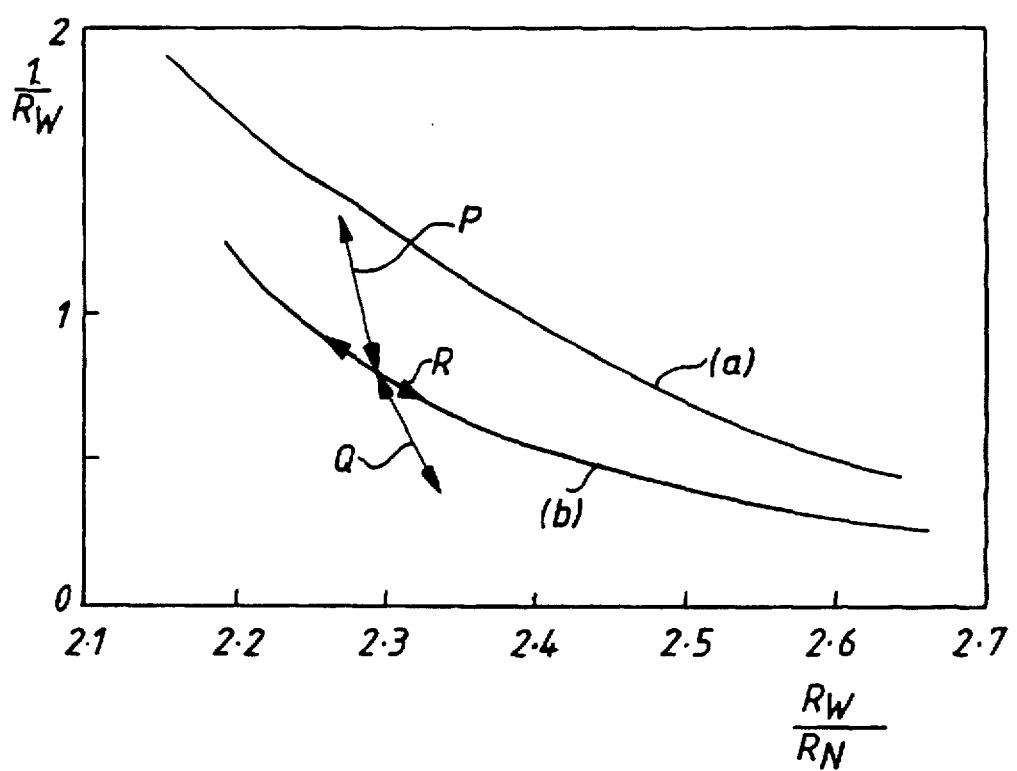
FIG. 5 shows operating lines for a sensor of the type exemplified in FIG. 1.

FIG. 5 gives an example of a steady-state operating line for an n-type semiconducting oxide sensor in a planar geometry (as in FIG. 1), having two electrode pairs only. In FIG. 5, $1/R_W$ is plotted against $R_W/R_N$, where $R_W$ and $R_N$, as before, are respectively the sensor resistance measured between the electrodes 14 and 16 of the widely spaced pair W, and between the electrodes 12 and 14 of the narrow pair N. The interferences which may, as stated above, be due to variations in oxygen partial pressure or ambient relative humidity, is modelled in this example as causing a doubling of the baseline conductance and an increase of 50% in the sensitivity to the gas. The assumed response law is that the conductance of the gas-sensitive material is proportional to the square root of the reactive gas concentration.

Such a model describes quite well the current experience concerning the response of tin dioxide elements to reactive gases such as carbon monoxide, present at concentrations up to a few hundred parts per million in the air. It also describes quite well the effect of an increase in ambient relative humidity from 0% to 100%. An operating line can be developed which allows the effect of the interferent to be distinguished from that of the reactive gas. If $R_N$ is plotted against $R_W$, then the slight shift in operating line is barely distinguishable, and the effect of the interferent could well be mistaken for an effect of change in the concentration of the reactive gas. If, however, an operating line is constructed by plotting the conductance $1/R_W$ against the ratio $R_W/R_N$ as in FIG. 5, then the effects of the two separate sources of variation can be readily distinguished.

Thus, in FIG. 5, the lines (a) and (b) are calculated operating lines for the sensor in two different conditions of relative humidity. The arrow P shows the shift of the operating point Y caused by a change in relative humidity for a given target gas concentration. The arrow Q shows the shift caused by poisoning of the device. The arrow R shows the effect of variation in target gas concentration at given relative humidity. The different patterns of variation will be clear.

Further information can clearly be gained from the variation, with time, of the position of the operating point, and this variation is of two types. The first is the variation of the steady-state operating point with time, this being variation on time scales that are long with respect to that required for the device to obtain a steady-state gas concentration profile within itself.

The second type of variation concerns the generalised non-steady-state operating line or surface according to the invention which has been described above, and which pertains more generally to gas-sensitive resistors than to those types in which the gas is decomposed upon diffusion through the sensor body.

One example of an application of this invention is a method of confirming the continued correct functioning of a multi-electrode sensor, by exposure of the sensor to a pulse of gas of ill-defined amplitude, such as may be applied from a can of gas in a field test. The point defined by the extreme resistance on one electrode pair and by the hysteresis in response between the different electrode pairs, is compared with the expected operating line or surface for the sensor.

In another example, natural variations in gas composition of an atmosphere are used in order to confirm the continuing correct operation of a sensor.

In use, a sensor will in general display a time-varying output as a consequence of the natural variation in composition of the atmosphere which is caused, for example, by the presence of people, or by someone smoking. These random variations of sensor response with time are analysed by Fourier transformation into the frequency domain. The transfer functions for the different electrode pairs are calculated as described above. The behaviour of the sensor in terms of amplitude, phase and frequency is compared with the expected operating surface for the sensor.

In a further example, the correct functioning of a multi-electrode sensor is tested with the aid of apparatus comprising a cover which fits over the sensor, so as to define an enclosed space around the latter, together with appropriate signal processing means and display means for indicating the test results. The apparatus also includes a bottle of a test gas which can be fitted on to the cover, the latter having an opening through which gas can be discharged into the interior of the cover, around the sensor, via an appropriate valve such as an electrically controlled solenoid valve carried by the gas bottle. The sensor mounting is of course provided with connections to enable the electrodes of the sensor to be connected to the processing means.

With the opening in the cover coupled to the solenoid valve, the latter is opened by suitable means in the apparatus, so introducing gas from the bottle to the sensor. When a change in a particular sensor resistance, e.g. that across the outer electrode pair 20 if the sensor is of the type shown in FIG. 4, is detected by the processing means (this change being of a pre-defined amount), the apparatus closes the solenoid valve, an indicator is activated, and the cover is opened to the atmosphere. The resistances across all the electrode pairs of the sensor are measured continuously during the whole test process.

The processing means determines the hysteresis and compares it with the expected value for the preset resistance change. If the preset resistance change is not achieved within a set time, or if the sensor hysteresis does not conform to that expected, then an indication of sensor failure is given. This system has the advantage of controlling to some degree the concentration of gas exposed to the sensor, and the variation of the gas pulse with time. Measurement of the hysteresis in the response between different electrode pairs permits the detection of incipient failure, such as failure by poisoning, or other factors which might lead to a loss of response. The system has the further advantage of applying a rigorous test without the need to obtain an accurately defined gas concentration.

It will be realised that, although the above description generally relates to the obtaining of information from sensors under non-steady state conditions, the method can be used even when prevailing operating conditions are in the steady state.

The signal processing means in which the operating lines or surface are defined, and which receive and process the signals from the sensor electrodes, relate the resulting information to the operating lines or surfaces and then make use of that relationship (in any desired way), are of any suitable kind consisting of readily-available standard equipment. Selection of suitable equipment, and any software for effecting the techniques provided by the invention, is well within the competence of any person ordinarily skilled in the design of gas sensing equipment. For that reason it has not been necessary to describe it here.

I claim:

1. A method of analysing a gaseous medium using a multiple-electrode resistive gas sensor of solid state semiconductor material comprising a resistor having an active surface and a plurality of pairs of electrodes, disposed on said resistor, each pair of said plurality of pairs of electrodes being different from each other pair of said plurality of pairs of electrodes as regards the spacing between the electrodes of the pair or the geometric orientation and disposition of the pair within the resistor relative to the active surface, the gaseous medium containing at least one target gas capable of causing electrical resistance of the sensor to vary in response to concentration of that gas, the method comprising: taking a resistance signal from each electrode pair with the sensor exposed to the gaseous medium; processing the signals to produce measurements therefrom; and relating the said measurements to a defined operating line or surface so as to determine, by deduction therefrom, a plurality of items of information, with the concentration of each target gas to be detected representing a separate said item of information, the number of electrode pairs being at least equal to the number of items of information to be obtained.

2. A method according to claim 1, including the correction of any error arising from the presence in the gaseous medium of a constituent that alters the sensor response, wherein each such error represents one item of information of said plurality of items of information to be obtained, so that the number of electrode pairs is at least equal to the number of target gases to be determined plus the number of said errors to be corrected for in said sensor response.

3. A method according to claim 2, including the step of deducing from the relationship between the said measurements and the defined operating line or surface a said error comprising a shift from the defined operating line or surface due to water vapour and/or ambient oxygen partial pressure in the said medium, the processing step including applying a correction to compensate for the relative humidity and/or ambient oxygen in the said medium and/or measurement thereof.

4. A method according to claim 1, including the step of deducing from the relationship between measurements and the defined operating line or surface a said error resulting from malfunction of the sensors, whereby the monitoring of the sensor comprises testing the sensor itself.

5. A method of monitoring a gas sensor comprising a gas-sensitive resistor of solid state semiconducting material having an active surface and a plurality of pairs of electrodes disposed on said resistor, each pair of said plurality of pairs of electrodes being different from each other pair as regards the spacing between the electrodes of the pair or the geometric orientation and disposition of the pair within the resistor relative to the active surface, the method comprising the steps of: defining an operating line or operating surface for the operation of the sensor in a gaseous medium at the active surface; exposing the sensor to a gaseous medium; processing the signals from each electrode pair that represent the resulting resistance of the resistor between the electrodes of that pair, so as to produce measurements therefrom defining an operating point; and relating the operating point to the defined operating line or surface, whereby the presence of an error in the detection of at least one gas in the said medium can be deduced from any shift of the operating point with respect to the defined operating line or surface, wherein the operating line or surface is defined for operation under non-steady state conditions, the sensor being exposed to the medium under non-steady or steady state conditions.

6. A method according to claim 5, wherein the signal processing step includes: processing first signals from a primary electrode pair; processing second signals from at least one secondary electrode pair; and computing the delay between the said first and second signals.

7. A method according to claim 6, wherein each signal is analysed into a set of sinusoidal variations, the delay being measured by computing from the said variations a transfer function for the or each secondary electrode relative to the primary electrode pair, the operating line or surface being defined at least partly in terms of the transfer functions.

8. A method according to claim 7, wherein the operating surface is defined as the expected variation of the amplitude and phase of the transfer functions of the different electrode pairs, as a function of frequency of variation in gas concentration to which the sensor is exposed.

9. A method according to claim 6, wherein a cross-correlation function is defined between the said first and second signals, the or each secondary electrode pair having a characteristic value of the said delay which is characteristic of that electrode pair, the cross-correlation function having a maximum value at the or each said characteristic value the operating line or surface being defined at least partly in terms of the said characteristic value or values.

10. A method according to claim 6, further including the step of applying a pulse of gas to the sensor, the signal processing step comprising measuring hysteresis between the said first signals and said second signals, the operating line or surface being defined by the magnitude of an extreme hysteresis value generated on at least one electrode pair as a function of an extreme value of the resistance signal from one electrode pair, so that an error resulting from sensor malfunction can be deduced from the relationship between the said measurements and the defined operating line or surface, whereby to test the sensor itself.

11. A method according to claim 10, for a sensor having a primary electrode and a plurality of secondary electrode pairs, wherein the operating surface is defined by the values of an extreme hysteresis value generated on each secondary electrode pair between the resistance signal from that pair and that from the primary pair, as a function of an extreme value of the resistance signal from the primary pair.

12. A method according to claim 1, wherein the signal processing step includes: processing first signals from a primary electrode pair; processing second signals from at least one secondary electrode pair; and computing the delay between the said first and second signals.

13. A method according to claim 12, wherein each signal is analysed into a set of sinusoidal variations, the delay being measured by computing from the said variations a transfer function for the or each secondary electrode pair relative to the primary electrode pair, the operating line or surface being defined at least partly in terms of the transfer functions.

14. A method according to claim 13, wherein the operating surface is defined as the expected variation of the amplitude and phase of the transfer functions of the different electrode pairs, as a function of frequency of variation in gas concentration to which the sensor is exposed.

15. A method according to claim 12, wherein a cross-correlation function is defined between the said first and second signals, the or each secondary electrode pair having a characteristic value of the said delay which is characteristic of that electrode pair, the cross-correlation function having a maximum value at the or each said characteristic value, the operating line or surface being defined at least partly in terms of the said characteristic value or values.

16. A method according to claim 12, wherein the signal processing step comprises measuring hysteresis between the said signals from different electrode pairs, the operating line or surface being defined by the magnitude of an extreme hysteresis value generated on at least one electrode pair as a function of an extreme value of the resistance signal from one electrode pair, so that an error resulting from sensor malfunction can be deduced from the relationship between the said measurements and the defined operating line or surface, whereby to test the sensor itself.

17. A method according to claim 16, for a sensor having a primary electrode pair and a plurality of secondary electrode pairs, wherein the operating surface is defined by the values of an extreme hysteresis value generated on each secondary electrode pair between the resistance signal from that pair and that from the primary pair, as a function of an extreme value of the resistance signal from the primary pair.

* * * * *